United States Patent
Zoidis

(10) Patent No.: US 6,555,822 B1
(45) Date of Patent: Apr. 29, 2003

(54) METHOD FOR IDENTIFICATION OF PLASTIC MATERIALS BY OPTICAL MEASUREMENTS

(75) Inventor: Evangelos Zoidis, Waiblingen (DE)

(73) Assignee: Sony International (Europe) GmbH, Berlin (DE)

( * ) Notice: Subject to any disclaimer, the term of this patent is extended or adjusted under 35 U.S.C. 154(b) by 222 days.

(21) Appl. No.: 09/626,659

(22) Filed: Jul. 27, 2000

(30) Foreign Application Priority Data

Jul. 29, 1999 (EP) .................................. 99114884

(51) Int. Cl.$^7$ .................................. G01J 3/00
(52) U.S. Cl. .................................. 250/341.1; 356/300
(58) Field of Search .................................. 356/300; 209/524; 250/341.1

(56) References Cited

U.S. PATENT DOCUMENTS 5,134,291 A * 7/1992 Ruhl, Jr. et al. ............ 250/341
5,318,172 A * 6/1994 Kenny et al. ............... 209/524
5,381,228 A   1/1995 Brace

FOREIGN PATENT DOCUMENTS

EP   0 607 048   7/1994

OTHER PUBLICATIONS

T.V. Karstang et al.: "Infrared Spectroscopy and Multivariate Calibration Used in Quantitative Analysis of Additives in High–Density Polyethylene" Chemometrics and Intelligent Laboratory Systems, vol. 14, No. 1–3, Apr. 1992, pp. 331–339, XP000274890.

* cited by examiner

Primary Examiner—John R. Lee
Assistant Examiner—Christoher M. Kalivoda
(74) Attorney, Agent, or Firm—Frommer Lawrence & Haug LLP; William S. Frommer; Dennis M. Smid

(57) ABSTRACT

Method for identification of plastic materials of interest by spectroscopic measurements, comprising the steps of measuring a sample and providing a sample spectrum; providing reference spectra for a given group of reference materials of interest, determining spectral distances between sample spectrum and reference spectra, material identification by associating the sample to the material having the reference spectrum with the smallest spectral distance to the sample spectrum. In this method a multi-level measurement is conducted, wherein in each level the number of possible materials is further limited. In a first level at least 2 sub-groups and in all levels starting with a second level at least one sub-group of possible materials are defined, wherein one sub-group in the first level comprises all possible materials that are easily distinguishable and at least one further sub-group in the first level comprises materials that are difficult to distinguish from each other. To each sub-group at least one identification frequency range is associated, and said spectral distances are only determined within said at least one identification frequency range in each relevant sub-group of each level and only with respect to reference spectra of materials being comprised in the relevant sub-group.

21 Claims, 1 Drawing Sheet

METHOD FOR IDENTIFICATION OF PLASTIC MATERIALS BY OPTICAL MEASUREMENTS

Figure 1:
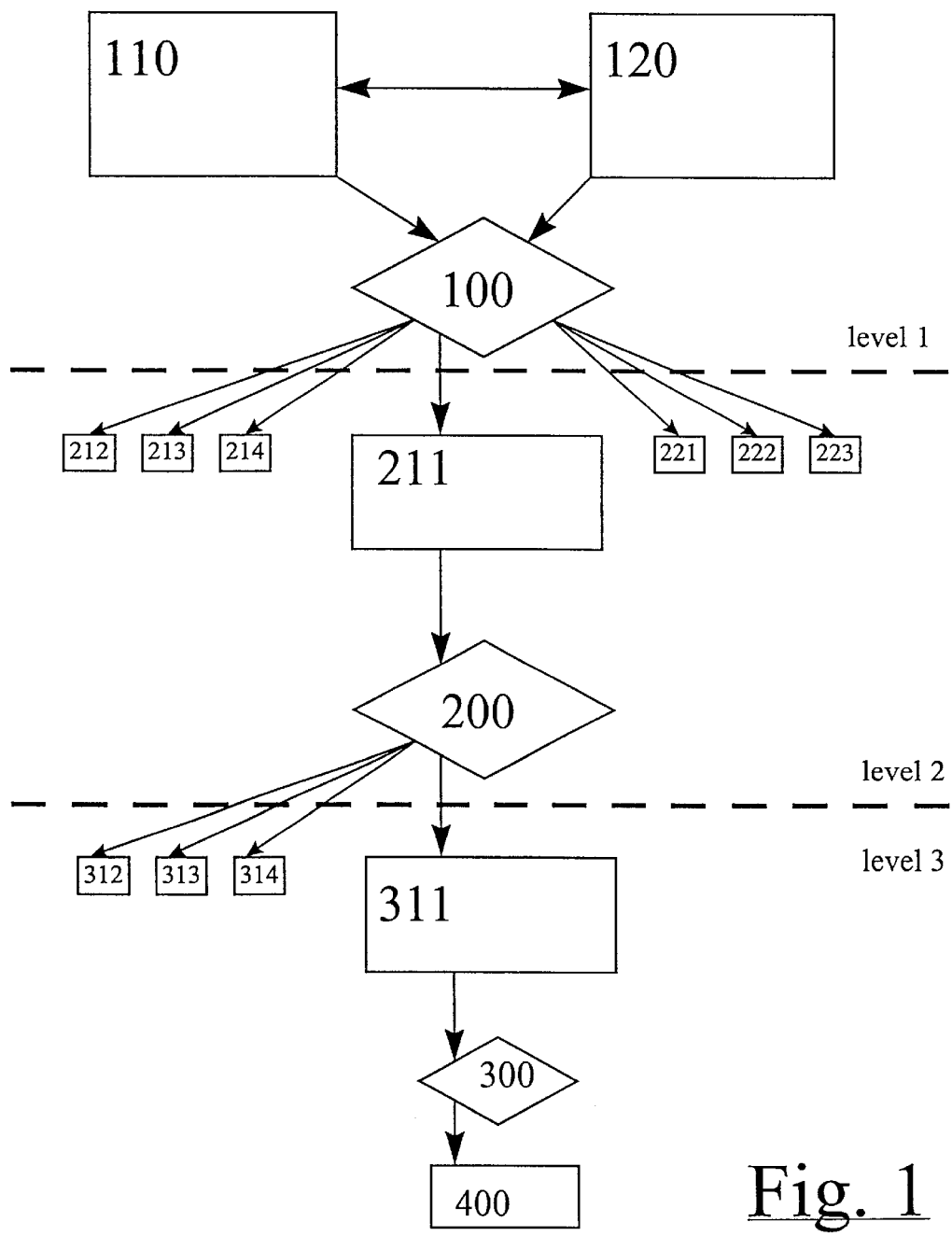

The present invention relates to a method for identification of different plastic materials by spectroscopy measurements.

Plastics industry has experienced a permanent global growth in the past decades and this tendency will be continued in the future, as plastic products are used for a lot of products, being sold in increasing numbers. Especially casings for computers, laptops, screens, televisions, packaging materials, interior elements and devices in cars as well as external automotive parts, furniture, casings for electronic devices etc. are manufactured from different plastic materials or even combinations thereof. The total plastic waste generated by the E&E sector was estimated to have reached 830.000 tons and is expected to increase up to 1.400.000 t in the year 2005.

With the increasing manufacturing of plastic and plastic products, disposal and recycling of such plastic products have become a problem for the environment. Therefore, it is desired to recycle most of the plastic materials.

For an effective recycling it is necessary that these plastic materials are identified and separated, as different materials require different and separated further treatments. One of the main problems occur in the use of flame retardant additives in plastic products to meet specific safety specifications. The percentage of plastics treated with flame retardants in "brown products" like TV sets is about 50%, whereas in the data processing equipment 100% of external parts of monitors are treated with flame retardants. These additives may be hazardous and therefore require specific environmental consideration and treatment for waste recovery.

As sorting and identification techniques, different methods are known in the art, using e.g. properties such as density, electrical, magnetical, tripological or chemical separation. But, there are similar polymers, like co-polymers or polymer blends, as well as materials with different additives that cannot be separated by these methods.

Especially with carbon filled (black) plastics, the identification of materials is very difficult and the identification rate is insufficiently low.

Therefore, optical measurements, especially spectroscopic techniques have been developed. Different techniques are known in the art, as e.g. Near Infrared Reflection (NIR), Mid-Infrared Reflection (MIR), MIR Pyrolysis, MIR Acousto-Optic Tunable Filters (AOTF), RAMAN Scattering, or others. Among the above mentioned techniques, NIR, MIR and RAMAN are the techniques with the best reliability for identification of plastic materials, as used in modem products.

With the above mentioned or other spectroscopic measurements, samples are measured and sample spectra as well as reference spectra for specific plastic materials are provided. Normally, the raw data, achieved by the spectroscopic measurement, are further prepared and/or processed, e.g. by performing a Fourier Transformation, a base line correction, a vector normalization, etc., in order to make a further comparison of reference spectra and sample spectra easier and more reliable. These preparations of raw data can be performed e.g. by means of a computer together with respective computer programs.

After a sample spectrum has been measured and prepared or processed, it will be compared to reference data of all plastic materials of interest. Spectral distances between the sample spectrum and between each reference spectrum is determined, whereas the sample is supposed to be of the material with the reference spectrum that shows the minimum spectral distance, ideally the spectral distance is equal to 0.

Because the number of plastic materials of interest is possibly very large, a lot of comparing steps of the sample spectra with each reference spectra over the whole frequency range, e.g. in MIR between 400 and 4000 cm$^{-1}$, is necessary. Such a procedure is very time consuming, and the correct identification ratio is unsufficiently low, as the measured and achieved spectral distances do not clearly distinguish for some possible materials of interest.

Especially for plastic materials containing flame retardants or additives, e. g. for coatings, the identification procedure of the state of art is not sufficiently reliable.

It is therefore an object of the present invention, to provide a method for identification of plastic materials of interest, wherein the procedure can be conducted in a less time consuming way and wherein more reliable results and therefore a higher correct identification rate can be achieved.

This object is achieved by a method according to claim 1. Claims 2 to 21 show preferred features of the inventive method of independent claim 1.

According to the invention a multi-level measurement is conducted, wherein in each level the number of possible materials is further limited. At least in the first level, there are defined at least two sub-group of possible materials, wherein one sub-group comprises all possible materials that are easily distinguishable from each other and at least one further group comprises materials that are difficult to distinguish from each other. To each sub-group there is at least one identification frequency range associated. This at least one identification frequency range is dependent on the possible materials of interest contained in the respective group. The spectral distances are only determined within said at least one identification frequency range and with respect only to the reference spectra of the materials being comprised in the respective sub-group.

By selecting and grouping possible materials of interest according to this invention, the spectral distances between sample spectra and reference spectra, necessary to be determined with a high resolution in order to reliably identify the sample material, can be determined, dependent on specific selected materials in a sub-group, only in frequency ranges, where spectral distances are present. Furthermore, spectral distances in "different directions" (plus/minus value), possibly leading to a nullification of the determinable spectral distance over the respective frequency range, can be avoided, thereby leading to extremely reliable identification results. Furthermore, the processing time for comparing sample spectra and reference spectra can be decreased, as only limited frequency ranges have to be taken into account.

The grouping and the association of specific identification frequency ranges to the respective sub-groups therefore leads both to a very high reliability and to very short identification times. Measurements with common plastic materials being used in most consumer products, including plastics with flame retardants and additives, did show identification results with a reliability of over 99% within a identification time of less than 1 second.

Preferably, the identification frequency ranges of each sub-group in one level have no frequency overlap. In addition, spectra appear only once in the respective sub-group. A clear distinction between frequency ranges, where spectral distances are relevant and measurable, taking into account the ratio between signal value and value differences and also taking into account noise of the measurements, from frequency ranges not showing a remarkable spectral distance, having an insufficient noise/signal or noise/signal-difference ratio, is achieved, thereby supporting reliability of the measurements.

With respect to mostly used and common plastic materials in consumer products, i. e.,the most important plastic materials of interest according to the invention, in the following there are given preferred groupings and identification frequency ranges as preferred realizations of the inventive method as claimed in claim 1 of the present invention.

For the sake of clarity, in the following there are given some short definitions for the terms used in the specification and in the claims: A "polymer" in the sense of this invention consists of an elementary (monomeric) unit and a chain. Such an elementary unit can be, for example, a styrene, wherein the chain can be an aliphatic chain. A "homo-polymer" in the sense of this invention consists only of one type of polymer, i. e. the same type of elementary unit and the same type of chain. Examples for such homo-polymers are PP (Polypropylene), PE (Polyethylene), PC (Polycarbonate), ABS (Acrylntril-Butadien-Styrol). "Hetero-polymers" consist of a mixture of two different types of polymers, i. e. a different type of elementary unit and/or a different type of chain. Examples for hetero-polymers are a blend of PC+ABS or a blend of HIPS (High Impact Polysterene) and PPO (Polypropylenoxide). "Single hetero-polymers" in the sense of this invention means hetero-polymers at a certain and not varying mixture ratio (within one goup or sub-group), e. g. a blend of PC+ABS with a mixture ratio of PC:ABS of 1:1. "Co-polymers" are belonging to a group of polymers, consisting of the same type of elementary unit, but with a different type of chain. There are co-polymers with styrene like HIPS, ABS, SAN or co-polymers with ethylene etc. "Single-co-polymer" in this invention means one polymer type of a certain class of co-polymers, like ABS, HIPS, SAN with styrene, as explained above.

Materials that are easily distinguishable in the sense of this invention are materials, which can be identified in one combined group with a sufficient reliability, dependent on the desired classification, i. e. whether it is desired only to identify for example the polymer types or also whether and which flame retardants and additives are incorporated in the material. What a "sufficient reliability" is, depends on the user of the method, in any case it should be over 95%.

Preferably, the group comprising materials easily distinguishable, has associated identification frequency ranges of 800–1420 $cm^{-1}$, 1620–2150 $cm^{-1}$, 2290–2780 $cm^{-1}$, and 3150–4000 $cm^{-1}$.

These frequency ranges ensure an identification of the polymer type of the sample, wherein the sample can be of the group comprising homo-polymers, single hetero-polymers, single copolymers, single homo-polymers with varying chain lengths, as PA6 or PA66, and homo-polymers with varying density with a reliability of over 99% in one combined group. Should the user be interested in whether there are flame retardants or coatings or additives present, further processing in a second level has to be conducted. To the preferred respective sub-groups and identification frequency ranges will be referred herein after.

For the at least one group comprising materials difficult to distinguish from each other, several groupings are preferred according to the invention. Depending on all possible materials of interest, it is possible that there are some of these sub-groups existing in parallel, but it is also possible that there is only one of these sub-groups existing besides the group with materials easily distinguishable.

One of these sub-groups preferably comprises co-polymers with or without flame retardants and/or additives. Such a group comprises for example the materials HIPS, ABS and SAN.

The preferred identification frequency ranges are 2150–2290 $cm^{-1}$ and 3000–3120 $cm^{-1}$.

Another of these sub-groups preferably comprises hetero-polymers with or without flame retardants and/or additives. This group is e. g. comprising blends of PC+ABS or HIPS+PPO in different relative proportions. HIPS+PPO is sometimes also referred to as HIPS+PPE (Polypropylenethyl), whereas normally the firstly mentioned compound is the one with a higher content. In this group, the relative proportions are not limited.

The preferred identification frequency ranges for such a sub-group comprising ABS and PC blends are 590–1000 $cm^{-1}$, 1040–1130 $cm^{-1}$, 1290–1480 $cm^{-1}$ and 1550–1750 $cm^{-1}$.

Another preferred group of materials difficult to distinguish comprises homo-polymers with varying chain lengths, for example polyamide 6, polyamide 66 or polyamide 12.

The preferred respective identification frequency range is 1090–1350 $cm^{-1}$.

In addition to these preferred groupings, certainly other groupings can be realized, e. g. a group comprising homo-polymers with varying density or polymers with special coatings. The method according to the invention and the inventive grouping and determination of identification frequency ranges is of course applicable also to materials not known at the time of the invention, for example further developed polymers with longer chains or specifics blends or other plastic materials. In case such a material not explicitly referred to in this specification is within the group of materials of interest and has to be identified, it is suggested according to the invention, to first try to fit the new material to one of the described sub-groups or to simply add another sub-group with materials difficult to distinguish from each other containing "other materials", e.g. these new materials.

The above described sub-groups and identification frequency ranges were preferably used in a first level of a preferred realization of the inventive method. Regarding further specified identification, taking especially into account flame retardants, further processing in further measurement levels is necessary. This is especially important, because materials with flame retardants require specific environmental consideration and treatment for recycling or waste recovery. About 16% of the total E&E plastic consumptions are modified with flame retardants, wherein the percentage of plastics treated with flame retardants in brown products like TV-sets is 50% and in the data processing equipment nearly 100% of external parts of monitors are treated with flame retardants.

Preferably, a second level of an embodiment of the inventive method therefore relates to identification of flame retardants in specific polymer types, already identified in the first level of the inventive method.

After the polymer material has been identified in a first level, in the second level it is preferably investigated, whether and which flame retardants or other additives are compounds of the sample material. The other additives could e.g. be plasticizers, fillers, stabilizers, colorants, anti-static agents, lubricants etc.

The preferred requirements for the identification frequency ranges, e.g. no frequency overlap and each spectra appearing only once in each sub-group, as explained above, are certainly also applicable for the sub-groups in levels other than the first level.

In case, HIPS has been identified in the first level, a preferred sub-group in the second level comprises HIPS with or without flame retardants. The preferred identification frequency ranges are in this case 800–1440 cm$^{-1}$, 1470–1480 cm$^{-1}$, 1700–1740 cm$^{-1}$.

In case ABS with or without flame retardants and/or additives or SAN have been identified in the first measurement level, a preferred identification frequency range in the second level for determining the kind of flame retardants are 800–1440 cm$^{-1}$, 1470 to 1480 cm$^{-1}$ and 1700–1720 cm$^{-1}$.

In case PC has been identified in the first level, for example as a member of a sub-group comprising material easily distinguishable, a preferred sub-group in the second level comprises PC with or without flame retardants and/or additives. The preferred associated identification frequency ranges are 590 to 1000 cm$^{-1}$, 1040–1130 cm$^{-1}$, 1290–1480 cm$^{-1}$ and 1550–1750 cm$^{-1}$.

In case PP (Polypropylene) has been identified, the associated identification frequency ranges are 590–940 cm$^{-1}$, 1020–1150 cm$^{-1}$, 1200–2280 cm$^{-1}$ and 2400–3500 cm$^{-1}$.

In case a blend of PC and ABS has been identified in the first level, the preferred respective identification frequency ranges for identification of flame retardants and/or additives are 590–1000 cm$^{-1}$, 1040–1130 cm$^{-1}$, 1290–1480 cm$^{-1}$ and 1550–1750 cm$^{-1}$.

The above-mentioned preferred identification frequency ranges are those frequency ranges showing a reliable and measurable spectral distance for the still possible materials of interest according to the respective level and the respective sub-group. Thereby a high reliability of identification can be achieved with a very short identification or processing time.

For determination of types of flame retardants, it is also possible to substrate the spectrum that has to be associated only with the polymer of the sample both to sample and reference spectra and to further process only the parts of the spectrum that arise from the respective flame retardants. Of course, it is also possible to directly provide reference spectra only of the flame retardants. Such a proceeding is within the scope of this inventive method.

Especially for identifications frequency ranges of specific groupings or sub-groups and also for groupings of newly developed materials, wherein the respective identification frequency ranges are not explicitly mentioned in the specification, it is preferred to determine identification frequency ranges having a high absolute deviation ratio D and/or a high smoothed deviation ratio D' between all pairs of possible plastic materials of interest that are still in the respective level and the respective sub-group for further processing.

The absolute deviation ratio reflects a ratio between the absolute signal distances of the spectra of two materials to be compared and the consistency or noise and is therefore an indicator for the reliability of the measurement at the respective frequency for these materials. The identification frequency ranges are therefore those areas, where the distance between the absolute signals of the respective spectra to be compared is very high on the one hand and the noise is very low on the other hand, thereby leading to a high reliability. The noise may be measured by means of a standard deviation, when measuring a certain number of samples with the same molecular origin, but also any other value for the noise or consistency of the measurements can be used.

It is especially preferred that the absolute deviation ratio D (X, Y, f), wherein X, Y are two of the possible plastic materials of interest, is determined by measuring a number N of different samples of the same molecular origin X, Y, numerically subtracting the N-weighted average of the measured signal F of the vibrational bands of sample Y from the N-weighted average of the measured signal F of the vibrational bands of sample X and normalizing by a term of the standard deviations or another value for the noise R of the sample X and Y measurements, wherein D is dependent of the measurement wavelength, the wavenumber or the frequency f.

The absolute deviation ratio is therefore determined according to the following formula:

$$D(X, Y, f) = \frac{[S(X, N, f) - S(Y, N, f)]}{[R(X, N, f) + R(Y, N, f)]}$$

It is further possible to determine a smoothed deviation ratio D' (X, Y, f) wherein this smoothed deviation ratio is the average value of the absolute deviation ration D (X, Y, f) within a wavenumber or frequency range of f−Δf and f+Δf. Δf is normally smaller than 40 cm$^{-1}$, preferably smaller than 20 cm$^{-1}$, further preferably smaller than 10 cm$^{-1}$.

When using the absolute deviation ratio D for the determination of identification frequency ranges, possibly a lot of interrupted or small frequency ranges will occur, whereas when using the smoothed deviation ratio D', the respective graph of deviation ratio will be smoother, thereby leading to wider frequency ranges. Using the absolute deviation ratio will lead to still more accurate results, whereas using the smoothed deviation ratio will simplify the measurement or the controlling of the respective measurement devices.

The spectral distance is, in accordance with the present invention, only determined within said at least one identification frequency range in each sub-group and in each level of the inventive method. Thereby also for new materials, not only the grouping and the association of the new product to a specific sub-group is within the scope of this invention, as explained above, but also determination of respective identification frequency ranges, in combination with the grouping and structure of the inventive method, leading to the desired high reliability and very fast processing times is disclosed and claimed in this specification.

Preferably the high absolute deviation ratio D and/or the high smoothed deviation ratio D' have a value of above +1 or below −1 for all pairs of possible materials of interest in the respective sub-group. With such a deviation ratio D or D', the desired reliability is ensured.

Only for completion, it should be mentioned that after the above-described two levels of measurements, identifying for example in the first level the polymer material, in the second level, whether there are flame retardants and which group of flame retardants, e. g. halogenated flame retardants or phosphated flame retardants, are components of the sample material, further levels can be added. For example in a third level the flame retardant type can be determined, in case the results from the second identification level are not specific enough for the user, although normally the second level results will be sufficient for all further treatment of the materials of interest.

After having e. g. identified halogenated flame retardants, it can be determined in the third level, which halogenated flame retardant is used. A sub-group in the third level can therefore e. g. comprise the identified polymer with HBCD (HexaBromoCycloDodecane), OBDO (OctaBromoDiphenylOxide), DBDE (DecaBromoDiphenylEther), TBBA (TetraBromoBisphenol-A), TBBB (TetraBromoBisphenol-(A) polyether), TBPE (1,2 bis-TetraBromoPhtalimide Ethane), PBBE (PentaBromoBenzylacrylate), EBPBD (Saytex 8010) and BTA (Brominated TriAzine).

In case of phosphated flame retardants, the preferred sub-group in the third level comprises TPP (TriPhenylPhosphate), TAP (TriAcrylPhosphat) and MC (Melamine Cyanurate).

It should therefore be understood that, on the basis of the disclosure of this specification, an artisan is capable of determining different structures with different levels and sub-groups having associated a specific identification frequency range.

The only accompanying drawing schematically showing as

FIG. 1 a structure of a preferred method according to the invention.

In FIG. 1 only two sub-groups 110, 120 are defined in a first level of the inventive method. The first sub-group 110 comprises materials easily distinguishable, in the specific case homo-polymers, single hetero-polymers, single homo-polymers with varying chain lengths and single homo-polymers with varying density or coated/painted materials.

The second sub-group 120 comprises materials difficult to distinguish from each other, in this specific case co-polymers with or without flame retardants or additives.

This structure is given by the group of possible materials that has to be identified. In this case there were no materials, not fitting in one of the two sub-groups 110, 120, especially there were no hetero-polymers or new materials to be taken into account for identification.

Measurement is first proceeded in this first level and in both sub-groups 110, 120. That means a sample material is first measured to provide a sample spectrum. The measurement resolution in this case was 10 cm$^{-1}$, in order to achieve optimum results. Sometimes also a resolution of 5 cm$^{-1}$ is realized. Of course, it is within the scope of this invention to adapt the measurement resolution to the materials to be identified as well as to the hardware and measurement systems used.

The sample spectrum is then compared with reference spectra that are present for all materials within the sub-groups, but only in the respective identification frequency ranges. Preferably the reference spectra show the same resolution as the corresponding sample spectra.

For the first sub-group 110, the respective identification frequency ranges are 800–1420 cm$^{-1}$, 1620–2150 cm$^{-1}$, 2290–2780 cm$^{-1}$ and 3150–4000 cm$^{-1}$. For the second sub-group 120, the identification frequency ranges are 2150–2190 cm$^{-1}$ and 3000–3120 cm$^{-1}$.

After the respective results of the spectral distances, it is possible to identify the sample polymer (identification step 100).

Based on this identification, the second level of the preferred inventive method is entered.

Depending on the identification of the first level, the respective next sub-group 211 in level 2, comprising the identified polymer, is selected for further processing. The other possible sub-groups 212, 213, 214, . . . and 221, 222, 223, . . . have not to be taken into account, as according to the identification of the first level, the sample material cannot be one of the materials comprised in these sub-groups.

Sub-group 211 comprises the identified polymer, in this case HIPS (High Impact Polysterene) with halogenated flame retardants, phosphated flame retardants or with other retardants or additives. The associated identification frequency ranges are 800 to 1440 cm$^{-1}$, 1470–1480 cm$^{-1}$ and 1700 to 1740 cm$^{-1}$.

After a determination of the spectral distance in these identification frequency ranges, the group of flame retardants is identified in identification step 200. The second level has therefore been finished.

It is now for example possible to stop the method, in case the identified information, i. e. the sample material is a HIPS with halogenated flame retardants, is sufficient for the user. In this case a 2-level measurement is realized.

In FIG. 1 on the other hand, a further level, a third level, is indicated for more specific identification of the material. In the sub-group 311 HIPS with different halogenated flame retardants, here HBCD, OBDO, DBDE, TBBA, TBBB, TBPE, PBBE, EBPBD, BTA are comprised. The other possible sub-groups 312, 313, and 314 have not been taken into account. After the identification step 300, the sample material 400 is identified including also flame retardant type. In this case the sample material was a HIPS with TBPE (1, 2 bisTetraBromo-PhtalimideEthane) as halogenated flame retardant.

Depending on the identified polymer, it is also possible in some cases that also the flame retardant type can be identified already in the second level, therefore the third level van be omitted.

It should be obvious to the artisan that the schematic diagram in FIG. 1 only shows a limited part of the structure of this preferred method, as many sub-groups in sub-levels of negatively identified materials have been omitted in order to increase clarity.

It should be also obvious to the artisan, especially in view of the above specification and explanations, that the structure of the preferred method is only one of lots of possible examples and realizations of the method according to the invention.

The features of the present invention disclosed in the specification, the claims and/or in the accompanying drawings may, both separately and in any combination thereof, the material for realizing the invention in various forms thereof.

What is claimed is:

1. Method for identification of plastic materials of interest by optical spectroscopic measurements, comprising the steps:

measuring a sample and providing a sample spectrum;

providing reference spectra for a given group of reference materials of interest, determining spectral distances between sample spectrum and reference spectra, material identification by associating the sample to the material having the reference spectrum with the smallest spectral distance to the sample spectrum, characterized in that a multi-level measurement is conducted, wherein in each level the number of possible materials is further limited, in a first level at least 2 sub-groups (110, 120) and in all levels starting with a second level at least one sub-group (211, 212, 213, 214, 221, 222, 223, 311, 312, 313, 314) of possible materials are defined, wherein one sub-group (110) in the first level comprises all possible materials that are easily distinguishable and at least one further sub-group (120) in the first level comprises materials that are difficult to distinguish from each other, to each sub-group (110, 120, 211, 212, 213, 214, 221, 222, 223, 311, 312, 313, 314) at least one identification frequency range is associated, and said spectral distances are only determined within said at least one identification frequency range in each relevant sub-group (110, 120, 211, 311) of each level and only with respect to reference spectra of materials being comprised in the relevant sub-group (110, 120, 211, 311).

2. Method according to claim 1, characterized in that the identification frequency ranges of each sub-group (110, 120; 211, 212, 213, 214, 221, 222, 223; 311, 312, 313, 314) in the same level have no frequency overlap.

3. Method according to claim 1, characterized in that one sub-group (110) comprising materials easily distinguishable from each other has associated identification frequency ranges of 800–1420 cm$^{-1}$, 1620–2150 cm$^{-1}$, 2290–2780 cm$^{-1}$ and 3150–4000 cm$^{-1}$.

4. Method according to claim 1, characterized in that said at least one sub-group (120), comprising materials difficult to distinguish from each other, comprises co-polymers with/without flame retardants and/or additives.

5. Method according to claim 4, characterized in that said at least one sub-group (120) comprises HIPS (High Impact Polysterene), ABS (Acryinitril-Butadien-Styrol) and SAN (Styrene-Acrylnitrile).

6. Method according to claim 4, characterized in that said at least one sub-group (120) has associated identification frequency ranges of 2150–2290 cm$^{-1}$ and 3000–3120 cm$^{-1}$.

7. Method according to claim 1 characterized in that said at least one sub-group, comprising materials difficult to distinguish from each other, comprises hetero-polymers with/without flame retardants and/or additives.

8. Method according to claim 7, characterized in that said at least one sub-group comprises PC (polycarbonate)+ABS (Acrylnitril-Butadien-Styrol) blend or HIPS (High Impact Polysterene)+PPO (Polypropyleneoxide) blend in different percentage proportions.

9. Method according to claim 7, characterized in that said at least one sub-group comprises PC+ABS blends and has associated identification frequency ranges of 590–1000 cm$^{-1}$, 1040 to 1130 cm$^{-1}$, 1290–1480 cm$^{-1}$ and 1550–1750 cm$^{-1}$.

10. Method according to claims 1, characterized in that said at least one sub-group, comprising materials difficult to distinguish from each other, comprises homo-polymers with varying chain lengths with/without flame retardants and/or additives.

11. Method according to claim 10, characterized in that said at least one sub-group comprises PA6 (Polyamide 6), PA66, PA12.

12. Method according to claim 10, characterized in that said at least one sub-group has an associated identification frequency range of 1090 to 1350 cm$^{-1}$.

13. Method according to claim 1, characterized in that said at least one sub-group, comprising materials difficult to distinguish from each other, comprises homo-polyimers with different density with/without flame retardants and/or additives.

14. Method according to claims 1, characterized in that said at least one sub-group, comprising materials difficult to distinguish from each other, comprises polymers with/without flame retardants and/or additives and with coatings.

15. Method according to claim 1, characterized in that one sub-group comprising HIPS (High Impact Polysterene) with/without flame retardants and/or additives is defined and identification frequency ranges of 800–1440 cm$^{-1}$, 1470 to 1480 cm$^{-1}$ and 1700–1740 cm$^{-1}$ are associated to this sub-group.

16. Method according to claims 1, characterized in that one sub-group comprising ABS (Acrylnitril-Butadien-Styrol) with/without flame retardants and/or additives or SAN (Styrene-Acrylnitrile) is defined and identification frequency ranges of 800–1440 cm$^{-1}$, 1470 to 1480 cm$^{-1}$ and 1700–1720 cm$^{-1}$ are associated to this sub-group.

17. Method according to claims 1, characterized in that one sub-group comprising PC (Polycarbonate) with/without flame retardants and/or additives is defined and identification frequency ranges of 590–1000 cm$^{-1}$, 1040 to 1130 cm$^{-1}$, 1290–1480 cm$^{-1}$ and 1550–1750 cm$^{-1}$ are associated to this sub-group.

18. Method according to claim 1, characterized in that one sub-group comprising PP (Polypropylene) with/without flame retardants and/or additives is defined and identification frequency ranges of 590–940 cm$^{-1}$, 1020 to 1150 cm$^{-1}$, 1200–1360 cm$^{-1}$ and 1520–1800 cm$^{-1}$ are associated to this sub-group.

19. Method according to claims 1, characterized in that one sub-group comprising PC (Polycarbonate)+ABS blend with/without flame retardants and/or additives is defined and identification frequency ranges of 590–1000 cm$^{-1}$, 1040 to 1130 cm$^{-1}$, 1290–1480 cm$^{-1}$ and 1550–1750 cm$^{-1}$ are associated to this sub-group.

20. Method according to claims 1, characterized in that said at least one identification frequency range of one of said sub-groups (110, 120, 211, 212, 213, 214, 221, 222, 223, 311, 312, 313, 314) has a high absolute deviation ratio or a high smoothed deviation ratio between all pairs of possible plastic materials of the respective sub-group (110, 120, 211, 212, 213, 214, 221, 222, 223, 311, 312, 313, 314).

21. Method according to claim 20, characterized in that the normalized value of the absolute deviation ratio or the smoothed deviation ratio is higher than 1 or lower than −1 for all pairs of possible materials of interest in the respective sub-group (110, 120, 211, 212, 213, 214, 221, 222, 223, 311, 312, 313, 314).

* * * * *